(12) United States Patent
Nakamura et al.

(10) Patent No.: US 9,000,367 B2
(45) Date of Patent: Apr. 7, 2015

(54) METHOD FOR EVALUATING POLYMER MATERIAL

(75) Inventors: Satoshi Nakamura, Kodaira (JP); Yuji Kurotani, Kodaira (JP); Tatsuro Tanabe, Kodaira (JP); Takaaki Igarashi, Kodaira (JP)

(73) Assignee: Bridgestone Corporation, Tokyo (JP)

(*) Notice: Subject to any disclaimer, the term of this patent is extended or adjusted under 35 U.S.C. 154(b) by 0 days.

(21) Appl. No.: 13/982,616

(22) PCT Filed: Feb. 8, 2012

(86) PCT No.: PCT/JP2012/052863
§ 371 (c)(1),
(2), (4) Date: Jul. 30, 2013

(87) PCT Pub. No.: WO2012/108465
PCT Pub. Date: Aug. 16, 2012

(65) Prior Publication Data
US 2013/0306865 A1    Nov. 21, 2013

(30) Foreign Application Priority Data
Feb. 8, 2011 (JP) .................................. 2011 024962

(51) Int. Cl.
*G01N 5/00* (2006.01)
*G01N 23/00* (2006.01)
(Continued)

(52) U.S. Cl.
CPC ................ *G01N 23/00* (2013.01); *G01N 1/286* (2013.01); *G01N 33/442* (2013.01)

(58) Field of Classification Search
CPC ......... G21K 5/00; G01N 1/286; G01N 23/00; G01N 33/44; G01Q 10/06; G01Q 20/04; G01Q 30/10; G01Q 60/12; G01Q 60/16

USPC .............. 250/306, 307, 309, 310, 311, 492.1, 250/492.2, 492.3
See application file for complete search history.

(56) References Cited

U.S. PATENT DOCUMENTS

| 5,770,861 A | 6/1998 | Hirose et al. |
| 2004/0262515 A1 | 12/2004 | Motoi et al. |

(Continued)

FOREIGN PATENT DOCUMENTS

| CN | 1849497 A | 10/2006 |
| EP | 1 209 737 A2 | 5/2002 |

(Continued)

OTHER PUBLICATIONS

International Search Report for PCT/JP2012/052863, dated Apr. 17, 2012.

(Continued)

*Primary Examiner* — Nicole Ippolito
*Assistant Examiner* — Hanway Chang
(74) *Attorney, Agent, or Firm* — Sughrue Mion, PLLC

(57) ABSTRACT

Provided is a method for evaluating a polymer material, wherein the state of dispersion of a filler in a polymer material can be quickly and quantitatively evaluated.

The method for evaluating a polymer material which is a polymer material containing the polymer compound and the filler and of which at least an upper surface is a flat surface. The polymer material 1 is cut in a direction at an angle α of 1 to 60° with respect to the surface of the polymer material using a focused ion beam (FIB) 10, and a smooth surface 1A of the polymer material, formed by the cutting, is then photographed in a direction perpendicular to the smooth surface.

4 Claims, 3 Drawing Sheets

(51) Int. Cl.
*G01N 1/28* (2006.01)
*G01N 33/44* (2006.01)

(56) References Cited

U.S. PATENT DOCUMENTS

2007/0051888 A1 3/2007 Rosenberg et al.
2011/0240905 A1* 10/2011 Funakubo et al. ............. 252/62

FOREIGN PATENT DOCUMENTS

| EP | 1 451 849 B1 | 12/2011 |
|---|---|---|
| JP | 59-41856 U | 3/1984 |
| JP | 05-087706 A | 4/1993 |
| JP | 09-115861 A | 5/1997 |
| JP | 11-045679 A | 2/1999 |
| JP | 3058394 B2 | 7/2000 |
| JP | 2003-194746 A | 7/2003 |
| JP | 2004-301639 A | 10/2004 |
| JP | 2005-259707 A | 9/2005 |
| JP | 2009-295371 A | 12/2009 |
| JP | 2010-286380 A | 12/2010 |

OTHER PUBLICATIONS

Communication dated Dec. 2, 2014 issued by the State Intellectual Property Office of the People's Republic of China in counterpart Chinese application No. 201280008199.1.

* cited by examiner (a)

(b)

(c)

(a)

(b)

(a)  (b)

(c)

METHOD FOR EVALUATING POLYMER MATERIAL

TECHNICAL FIELD

The present invention relates to a method for evaluating a polymer material (hereinafter also simply referred to as "evaluation method") and more particularly relates to a polymer material evaluating method for evaluating the state of dispersion of a filler in a polymer material containing a polymer compound and the filler.

BACKGROUND ART

Conventionally, a technique called FIB-SEM, as illustrated in FIG. 4, has been known as a technique for evaluating the state of dispersion of a filler in a polymer material containing a polymer compound and the filler. In the technique as illustrated, first, (a) a polymer material 1 is irradiated with a focused ion beam (FIB) 10 in a perpendicular direction; and (b) the surface of the polymer material 1 is cut. Then, (c) a smooth cut surface 1B which is parallel to a beam direction in the cut surface formed by the cutting is photographed by a scanning electron microscope (SEM), and the state of dispersion of the filler is evaluated by observing an obtained image. A technique called 3D-TEM as illustrated in FIG. 5 is also known.

In the above, FIB-SEM is a technology that is frequently used for, e.g., the cross-section observation of the wiring situation of a semiconductor; and, in this case, since the resolution of the semiconductor in its thickness direction is very important, it is necessary to irradiate the semiconductor with FIB in the thickness direction. Further, for example, Patent Document 1 discloses, as an improved technology for a method for observing the state of dispersion of a silica blended in a silicone rubber by an electron microscope, a method for observing dispersion of a silica in a silicone rubber, comprising: freezing and curing a molded product of a silicone rubber blended with a silica; then tearing the product to make a sample; and observing the torn surface of the sample by a scanning electron microscope set at a low acceleration voltage of 10 kV or less.

RELATED ART DOCUMENT

Patent Document

Patent Document 1: Japanese Unexamined Patent Application Publication No. 5-87706 (Claims, etc.)

SUMMARY OF THE INVENTION

Problems to be Solved by the Invention

The cross-sectional image of a polymer material can be observed and evaluated by FIB-SEM or 3D-TEM. However, in conventional FIB-SEM, the cut surface of a polymer material has been inevitably observed in a diagonal direction, the brightness levels in the upper and lower parts of an image have been different, the image has been out of focus, and, therefore, the state of dispersion of a filler in a polymer material has not been able to be quantitatively evaluated as the whole image. Further, 3D-TEM has had a drawback that quantitative evaluation necessitates enormous time although the quantitative evaluation is possible. Accordingly, it has been desired to establish such an index representing the state of dispersion of a filler that the quick and quantitative evaluation of the whole image is enabled and an explanation can be given on the physical properties of a polymer material containing the filler.

Thus, an object of the present invention is to solve the above-described problems to provide a method for evaluating a polymer material, wherein the state of dispersion of a filler in a polymer material can be quickly and quantitatively evaluated.

Means for Solving the Problems

As a result of extensive examination, the present inventors found that the direction of irradiation of a polymer material with a focused ion beam is made to be a direction at an angle of 1 to 60° with respect to the surface thereof and the cross-sectional image of the polymer material is photographed in a direction perpendicular to a surface to be photographed to allow the above-described problems to be solved, and the present invention was thus accomplished.

In other words, the present invention is a method for evaluating a polymer material containing a polymer compound and a filler, of which at least an upper surface is a flat surface, the method comprising:

cutting the upper surface of the polymer material in a direction at an angle of 1 to 60° with respect to the upper surface of the polymer material using a focused ion beam; and then photographing a smooth surface of the polymer material, formed by the cutting, in a direction perpendicular to the smooth surface.

In accordance with the present invention, it is preferable to photograph the smooth surface of the polymer material using a scanning electron microscope. Further, examples of the filler include at least one selected from the group consisting of silicas, carbon blacks, and inorganic compounds represented by the following formula:

$$mM \cdot xSiO_y \cdot zH_2O \qquad (I)$$

(wherein M is at least one selected from metals selected from the group consisting of aluminum, magnesium, titanium, calcium and zirconium, oxides or hydroxides of the metals and hydrates thereof, or carbonates of the metals; and m, x, y, and z are an integer of 1 to 5, an integer of 0 to 10, an integer of 2 to 5, and an integer of 0 to 10, respectively). Furthermore, in accordance with the present invention, an image obtained by photographing the smooth surface of the polymer material is converted into a binarized image of a polymer compound section and a filler section, and the state of dispersion of the filler in the polymer material can be evaluated based on the obtained binarized image.

Effects of the Invention

According to the present invention, the above-described constitution enables the detection of the high-precision image of the cross section of a polymer material, which can be converted into numbers, and, as a result, there can be realized a method for evaluating a polymer material, wherein the state of dispersion of a filler in a polymer material can be quickly and quantitatively evaluated.

MODE FOR CARRYING OUT THE INVENTION

Embodiments of the present invention will be explained in detail below with reference to the drawings.

The present invention relates to the improvement of a method for evaluating a polymer material which contains a polymer compound and a filler and of which at least an upper surface is a flat surface.

Figure 1:
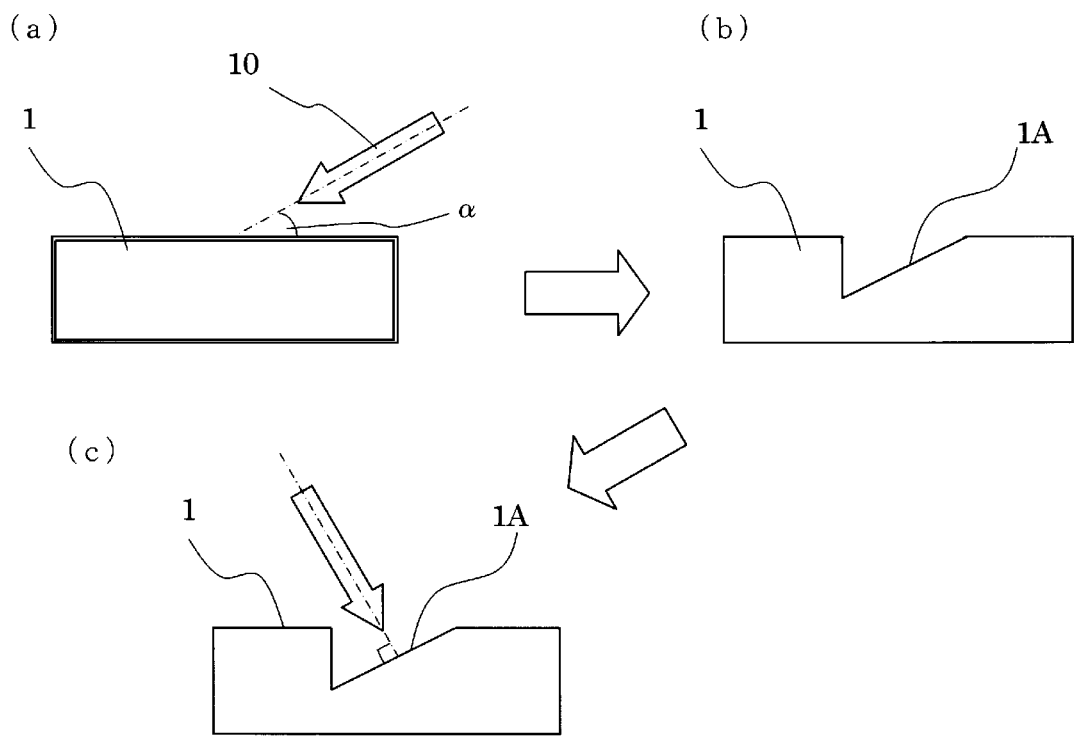
FIGS. 1(a) to (c) are explanation views that illustrate an example of the method for evaluating a polymer material of the present invention.

In FIG. 1, there are illustrated explanation views that illustrate an example of the method for evaluating a polymer material of the present invention. As illustrated in the drawing, in accordance with the present invention, first, (a) the upper surface of a polymer material 1 is cut in a direction at an angle α of 1 to 60° with respect to the upper surface of the polymer material 1 using a focused ion beam (FIB) 10. Then, (b) the smooth surface 1A of the polymer material 1, formed by the cutting, is (c) photographed in a direction perpendicular to the smooth surface 1A.

As for the flat cross section of the polymer material, a high-precision image containing only the surface information of the cross section can be captured without any influence such as a difference in brightness between the upper and lower sections of an image or an out-of-focus image as in a conventional technique by cutting the surface of the polymer material 1 in the direction of inclination at a certain angle with respect to the surface to photograph the smooth surface 1A in the exposed cut surface in a perpendicular direction in such a manner. As a result, the physical property of the polymer material containing a filler can be quantitatively evaluated by converting the state of dispersion of the filler in the polymer material into numbers based on the obtained high-precision image. In addition, when the polymer material 1 is cut by FIB 10, a cut surface formed in a direction parallel to the direction of irradiation with FIB 10 becomes a smooth surface without recesses and projections while a cut surface formed in a direction perpendicular to the direction of irradiation with FIB 10 becomes a rough surface having recesses and projections. Accordingly, the smooth surface 1A to be photographed in the present invention means the cut surface formed in the direction parallel to the direction of the irradiation with FIB 10.

In accordance with the present invention, as photographing means for photographing the smooth surface 1A of the polymer material 1, which photographing means may be any means, a scanning electron microscope (SEM), a helium ion microscope, or the like may be used, and SEM is preferably used. Particularly, a high-precision cross-sectional image can be obtained by photographing only an outermost surface in the smooth surface 1A by low-acceleration SEM at an acceleration voltage of 5 kV or less. Specifically, for example, the above-described polymer material can be efficiently cut and photographed by using commercially available FIB-SEM, e.g., NOVA 200 manufactured by FEI Company. In other words, by FIB-SEM, the surface of the polymer material 1 can be cut in a specified inclination direction to obtain the smooth surface 1A and can be then photographed in a perpendicular direction without changing the angle of the smooth surface 1A, and a high-precision image with the optimal contrast and focus of the whole image can be easily obtained.

The polymer material that can be evaluated in the present invention may be any material as long as the polymer material contains a polymer compound and a filler. Specifically, for example, the polymer material is prepared by dispersing, in a polymer compound such as a synthetic resin or a rubber, a filler comprising at least one selected from the group consisting of silicas, carbon blacks, and certain inorganic compounds; and, in accordance with the present invention, the state of dispersion of a filler in such a polymer material can be quantitatively evaluated.

The synthetic resin may be any of thermosetting resins and thermoplastic resins or may be a mixture of two or more thereof. Examples of the thermosetting resins include epoxy resins, diallyl phthalate resins, silicone resins, phenolic resins, unsaturated polyester resins, polyimide resins, polyurethane resins, melamine resins, urea resins, and the like. Further, examples of the thermoplastic resins may include polyethylene, polypropylene, polyamide, polystyrene, polycarbonate, polybutylene terephthalate, polyethylene terephthalate, polyphenylene sulfide, polyacetal, polyphenylene oxide, polyethersulfone, polyetherimide, polyether ether ketone, polymethyl methacrylate, polyacrylonitrile, and the like. Furthermore, examples of the rubber may include natural rubber, styrene-butadiene rubber, butadiene rubber, isoprene rubber, chloroprene rubber, butyl rubber, halogenated butyl rubber, ethylene-propylene rubber, acrylic rubber, chlorosulfonated polyethylene rubber, and the like, which may be used alone or as a mixture.

Examples of the silicas include wet silica (hydrous silicic acid) and dry silica (silicic anhydride). Further, examples of the carbon blacks include FEF, GPF, SRF, HAF, N339, IISAF, ISAF, SAF, and the like. Furthermore, examples of the inorganic compounds include inorganic compounds represented by the following formula:

$$mM \cdot xSiO_y \cdot zH_2O \tag{I}$$

(wherein M is at least one selected from metals selected from the group consisting of aluminum, magnesium, titanium, calcium and zirconium, oxides or hydroxides of the metals and hydrates thereof, or carbonates of the metals; and m, x, y, and z are an integer of 1 to 5, an integer of 0 to 10, an integer of 2 to 5, and an integer of 0 to 10, respectively). Specific examples of such inorganic compounds include alumina ($Al_2O_3$) such as γ-alumina or α-alumina, alumina monohydrate ($Al_2O_3 \cdot H_2O$) such as boehmite or diaspore, aluminum hydroxide [$Al(OH)_3$] such as gibbsite or bayerite, aluminum carbonate [$Al_2(CO_3)_2$], magnesium hydroxide [$Mg(OH)_2$], magnesium oxide (MgO), magnesium carbonate ($MgCO_3$), talc ($3MgO \cdot 4SiO_2 \cdot H_2O$), attapulgite ($5MgO \cdot 8SiO_2 \cdot 9H_2O$), titanium white ($TiO_2$), titanium black ($TiO_{2n-1}$), calcium oxide (CaO), calcium hydroxide [$Ca(OH)_2$], aluminum magnesium oxide ($MgO \cdot Al_2O_3$), clay ($Al_2O_3 \cdot 2SiO_2$), kaoline ($Al_2O_3 \cdot 2SiO_2 \cdot 2H_2O$), pyrophyllite ($Al_2O_3 \cdot 4SiO_2 \cdot H_2O$), bentonite ($Al_2O_3 \cdot 4SiO_2 \cdot 2H_2O$), aluminum silicate ($Al_2SiO_5$, $Al_4 \cdot 3SiO_4 \cdot 5H_2O$, or the like), magnesium silicate ($Mg_2SiO_4$, $MgSiO_3$, or the like), calcium silicate ($Ca_2 \cdot SiO_4$ or the like), aluminum calcium silicate ($Al_2O_3 \cdot CaO \cdot 2SiO_2$ or the like), magnesium calcium silicate ($CaMgSiO_4$), calcium carbonate ($CaCO_3$), zirconium oxide ($ZrO_2$), zirconium hydroxide [$ZrO(OH)_2 \cdot nH_2O$], zirconium carbonate [$Zr(CO_3)_2$], crystalline aluminosilicates containing hydrogen, an alkali metal or an alkaline earth metal each compensating a charge, as is the case with various zeolites, and the like.

It is necessary for determining the direction of irradiation with FIB 10 and the direction of photographing that at least the upper surface is approximately flat as the shape of the polymer material, and, preferably, a shape in which the upper and lower surfaces are flat as illustrated in the drawings, particularly a rectangular parallelepiped shape, may be used.

In accordance with the present invention, in order to convert the state of dispersion of the filler in the polymer material into numbers based on the high-precision image obtained as described above, first, the image is converted into a binarized image of polymer compound sections and filler sections according to a light/shade difference. Then, the state of dispersion of the filler in the polymer material can be evaluated by, for example, determining the aggregate area of the filler sections based on the obtained binarized image. In other words, since the filler is present in the state of aggregates prepared by aggregating the filler in the polymer material, the area of each of the aggregates corresponding to the filler sections in the binarized image is determined, and the average aggregate area of the filler sections is calculated from the obtained total surface area of the filler sections and the number of the filler aggregates and can be thus made to be an index of the state of the dispersion of the filler as the physical property of the polymer material. Conventionally, the state of dispersion of a filler has been inevitably evaluated only by visual observation of an unclear image, but, according to the invention, the state of dispersion of a filler can be quantitatively evaluated and predicted with high precision by certain parameters. The smaller the average aggregate area of the filler is, the better the state of the dispersion of the filler is.

The present invention is useful in development of various filler-containing polymers and can be applied to, in addition, the various fields of development support related to a polymer material containing a polymer compound and a filler, such as development of a silane coupling agent, development of silica, and development of a rubber milling technology.

EXAMPLES

The present invention will be explained in more detail below with reference to examples.

<Preparation of Rubber Composition>

In a 1.8-liter Banbury mixer, 110 parts by mass of diene rubber ("#1712", manufactured by Japan Synthetic Rubber Co., Ltd.) and 20 parts by mass of natural rubber were masticated at 70 rpm and a starting temperature of 80° C. for 30 seconds, the resultant was blended with 20 parts by mass of ISAF grade carbon black ("SEAST 7HM", manufactured by Tokai Carbon Co., Ltd.), 50 parts by mass of silica ("Nipsil AQ", manufactured by Nippon Silica Industries Co., Ltd.), 1 part by mass of stearic acid, 1 part by mass of an age resistor 6PPD (N-phenyl-N'-(1,3-dimethylbutyl)-p-phenylenediamine), and 6.3 phr (blending amount based on 100 parts by mass of a rubber component) of a silane coupling agent ("Si69", manufactured by Degussa AG), and the blend was kneaded, until it became at 160° C., was then released, and was formed into a sheet shape by a roll. Then, the remilling operation of the resultant was carried out in the 1.8-liter Banbury mixer at 70 rpm and a starting temperature of 80° C. for 1 minute 30 seconds, was then released, and was formed into a sheet shape by the roll. The resultant was sufficiently cooled to room temperature and was then mixed with 3 parts by mass of active zinc, 0.5 part by mass of vulcanization accelerator DM (dibenzothiazyl disulfide), 1.0 part by mass of vulcanization accelerator NS (N-t-butyl-2-benzothiazylsulfenamide), and 1.5 parts by mass of sulfur, and the mixture was kneaded at 60 rpm and a starting temperature 80° C. for 1 minute to obtain a rubber composition.

Example

The state of dispersion of silica in the rubber composition obtained as described above was evaluated using FIB-SEM (NOVA 200 manufactured by FEI Company). An evaluation sample was produced by cutting a rubber sheet with a razor. The shape of the sample was in 5 mm×5 mm×1 mm in thickness.

Figure 2:
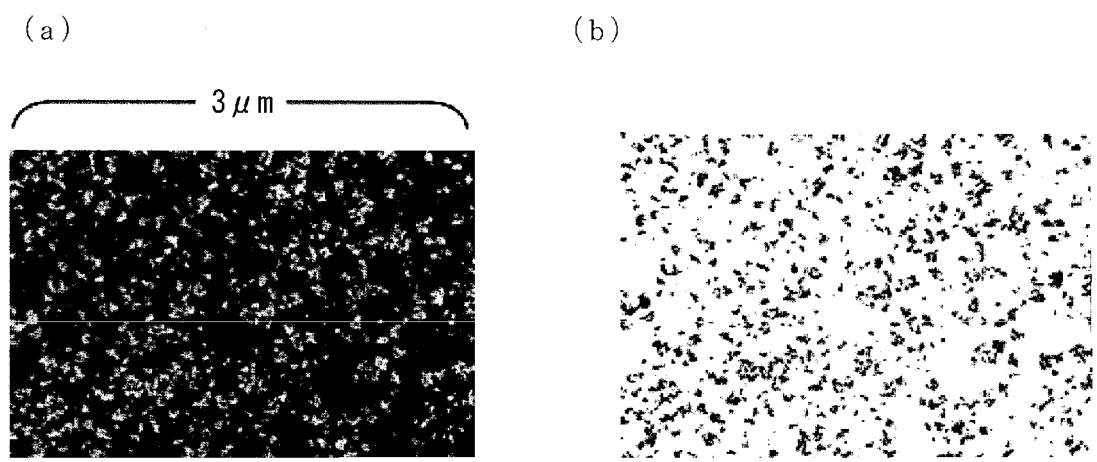
FIG. 2(a) is a photograph view that illustrates an example of an image obtained in Example.
FIG. 2(b) is a photograph view that illustrates an image obtained by binarizing the image in (a).

As illustrated in FIG. 1, first, the sample was cut in a direction at an angle $\alpha$ of 38° with respect to a sample surface using FIB 10 under the condition of a voltage of 30 kV. Then, the smooth surface 1A of the sample, formed by the cutting, was photographed in a direction perpendicular to the smooth surface 1A using SEM at a low acceleration voltage which was an acceleration voltage of 5 kV or less. The obtained image contained only the information of the outermost surface section of the smooth surface 1A. An example of the obtained image is illustrated in FIG. 2(*a*).

Then, the obtained image was converted into a binarized image of a rubber section which was a polymer compound and a silica section which was a filler according to a usual method. The image obtained by binarizing the image illustrated in FIG. 2(*a*) is illustrated in FIG. 2(*b*). Based on the obtained binarized image, the aggregate area of silica sections was determined using an image analysis software, and the average aggregate area of the silica sections per unit area was calculated from the total surface area of the silica sections and the number of silica aggregates.

Then, the average aggregate areas of four rubber compositions prepared by intentionally changing the state of dispersion of silica by changing the rubber milling conditions were calculated by the same procedure as described above. Further, the storage elastic modulus ($\Delta G'$) of each rubber composition was measured as described below.

The storage elastic modulus (G') of vulcanized rubber obtained by vulcanizing each of the above-described rubber compositions under the conditions of 145° C. and 30 minutes was measured using an ARES viscoelasticity testing apparatus manufactured by Rheometric Scientific, Inc. under the conditions of 20° C., 10 Hz, and strains of 0.25% and 14% under a shear input to calculate $\Delta G'=(0.25\% \text{ E})-G' (14.0\% \text{ E})$.

Figure 3:
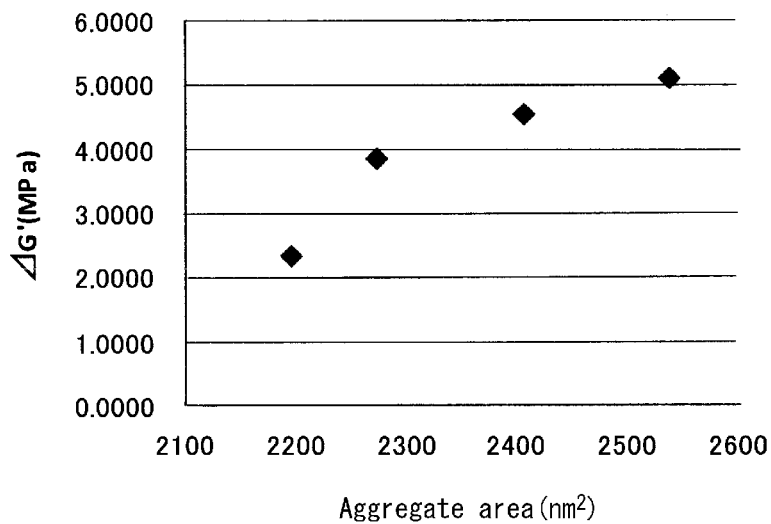
FIG. 3 is a graph that indicates a correlation between an average aggregate area and a storage elastic modulus (ΔG') in Example.

As a result, the average aggregate area correlated with the value of the storage elastic modulus ($\Delta G'$) as indicated in the graph of FIG. 3. Therefore, the average aggregate area was confirmed to correlate with the physical property of rubber as an index of the state of dispersion of a filler. For example, when the dispersion state was intentionally changed by changing of the kind of the silane coupling agent, a similar correlation was also confirmed to be provided.

Conventional Example 1

Figure 4:
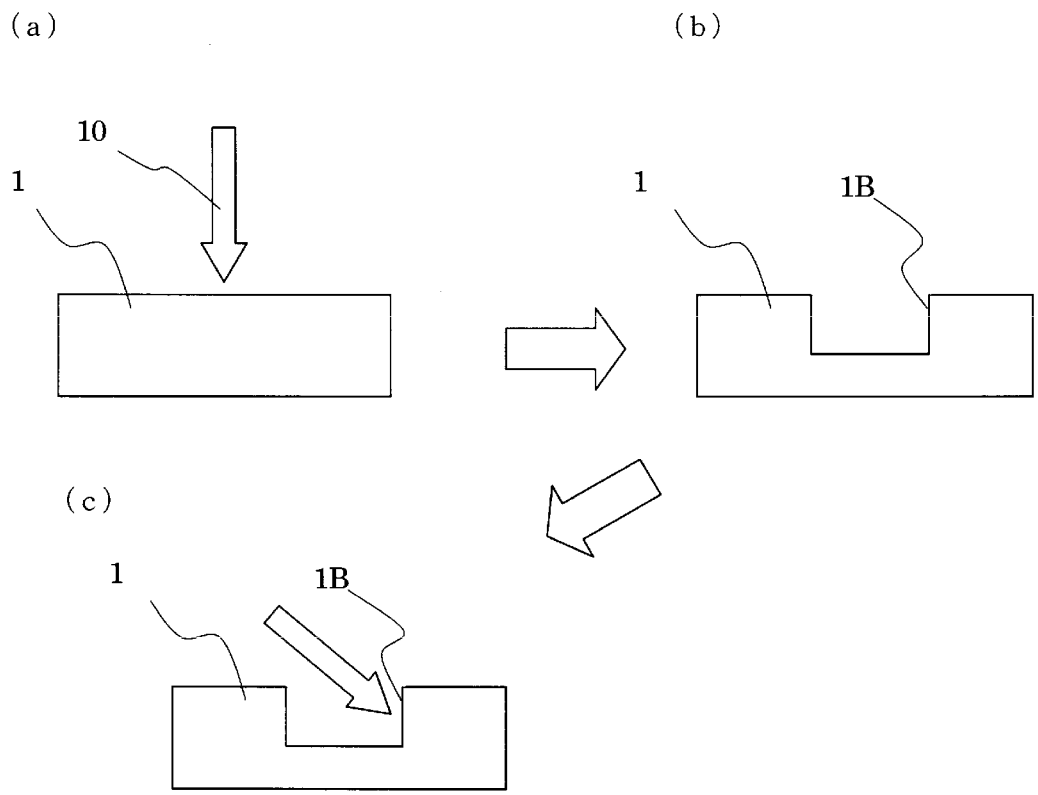
FIGS. 4(a) to (c) are explanation views that illustrate an example of an evaluation method using conventional FIB-SEM.

Using a rubber composition sample (dimension: 5 mm×5 mm×1 mm in thickness) similar to the sample used in the above-described example, first, the sample was irradiated with FIB 10 in a perpendicular direction as illustrated in FIGS. 4(*a*) and (*b*) to cut a sample surface. Then, the smooth surface 1B of the sample, formed by the cutting, was photographed using SEM in a direction at 52° with respect to the smooth surface 1B in the same manner as in Example, as illustrated in FIG. 4(*c*). When the obtained image was observed, brightness and a focus differed between the upper and lower sections of the photograph since the photographing was performed diagonally with respect to the photographed surface, so that the image was not such a high-precision image as to be able to be binarized. Thus, only the visual observation of the image was performed to finish this example, and the image was not converted into numbers.

Conventional Example 2

Figure 5:
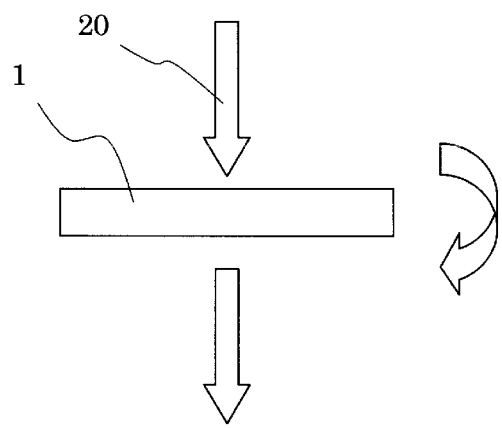
FIG. 5 is a explanation view that illustrates an example of an evaluation method using conventional 3D-TEM.

Using a rubber composition sample (dimension: 0.5 mm×0.5 mm×about 200 nm in thickness) similar to the sample used in the above-described example, observation by 3D-TEM was performed as illustrated in FIG. 5. Specifically, as illustrated in the drawing, the sample was rotated while irradiating the sample with an electron beam 20, shadow pictures at various angles were photographed, and an image was made by 3D-construction by a computer. As a result, the high-precision image was obtained; however, since the capture of the image took around 2 days per sample and was time-consuming, this technique was too time-consuming to use as an analytical technique for development support.

REFERENCE SIGNS LIST

1 Polymer material
1A, 1B Smooth surface
10 FIB
20 Electron beam

The invention claimed is:

1. A method for evaluating a polymer material containing a polymer compound and a filler, of which at least an upper surface is a flat surface, the method comprising:
cutting the upper surface of the polymer material in a direction at an angle of 1 to 60° with respect to the upper surface of the polymer material using a focused ion beam; and then photographing a smooth surface of the polymer material, formed by the cutting, in a direction perpendicular to the smooth surface, and
wherein the filler is at least one selected from the group consisting of silicas, carbon blacks, and inorganic compounds represented by the following formula (I):

$$mM \cdot xSiO_y \cdot zH_2O \qquad (I)$$

(wherein M is at least one selected from metals selected from the group consisting of aluminum, magnesium, titanium, calcium and zirconium, oxides or hydroxides of the metals and hydrates thereof, or carbonates of the metals; and m, x, y, and z are an integer of 1 to 5, an integer of 0 to 10, an integer of 2 to 5, and an integer of 0 to 10, respectively).

2. The method for evaluating a polymer material according to claim 1, wherein the smooth surface of the polymer material is photographed using a scanning electron microscope.

3. The method for evaluating a polymer material according to claim 2, wherein an image obtained by photographing the smooth surface of the polymer material is converted into a binarized image of a polymer compound section and a filler section, and the state of dispersion of the filler in the polymer material is evaluated based on the obtained binarized image.

4. The method for evaluating a polymer material according to claim 1, wherein an image obtained by photographing the smooth surface of the polymer material is converted into a binarized image of a polymer compound section and a filler section, and the state of dispersion of the filler in the polymer material is evaluated based on the obtained binarized image.

* * * * *